(12) United States Patent
Moggridge et al.

(10) Patent No.: US 12,201,744 B2
(45) Date of Patent: Jan. 21, 2025

(54) HEART VALVE

(71) Applicant: CAMBRIDGE ENTERPRISE LIMITED, Cambridge (GB)

(72) Inventors: Geoff Moggridge, Cambridge (GB); Joanna Stasiak, Cambridge (GB); Jacob Brubert, Cambridge (GB)

(73) Assignee: CAMBRIDGE ENTERPRISE LIMITED, Cambridge (GB)

( * ) Notice: Subject to any disclaimer, the term of this patent is extended or adjusted under 35 U.S.C. 154(b) by 1260 days.

(21) Appl. No.: 16/833,570

(22) Filed: Mar. 28, 2020

(65) Prior Publication Data

US 2021/0085824 A1 Mar. 25, 2021

Related U.S. Application Data

(63) Continuation of application No. 15/122,116, filed as application No. PCT/GB2015/050346 on Feb. 9, 2015, now abandoned.

(30) Foreign Application Priority Data

Feb. 27, 2014 (GB) ..................... 1403454

(51) Int. Cl.
| | | |
|---|---|---|
| *A61L 27/16* | (2006.01) | |
| *A61F 2/24* | (2006.01) | |
| *A61L 27/50* | (2006.01) | |
| *B29C 45/00* | (2006.01) | |

(Continued)

(52) U.S. Cl.
CPC .......... *A61L 27/16* (2013.01); *A61F 2/2412* (2013.01); *A61F 2/2415* (2013.01); *A61L 27/50* (2013.01); *B29C 45/0001* (2013.01); *A61F 2240/001* (2013.01); *A61F 2250/0018* (2013.01); *A61L 2430/20* (2013.01); *B29C 2045/0098* (2013.01); *B29K 2096/04* (2013.01); *B29L 2031/7534* (2013.01)

(58) Field of Classification Search
CPC .......... A61F 2/2412; A61F 2250/0018; A61L 27/16; A61L 27/50; A61L 2430/20
See application file for complete search history.

(56) References Cited

U.S. PATENT DOCUMENTS

| | | |
|---|---|---|
| 5,622,668 A | 4/1997 | Thomas et al. |
| 8,092,818 B2 | 1/2012 | Richard et al. |

(Continued)

FOREIGN PATENT DOCUMENTS

| | | |
|---|---|---|
| EP | 2208518 A2 | 7/2010 |
| EP | 2200672 B1 | 6/2012 |

(Continued)

OTHER PUBLICATIONS

Fang et al., "Surface morphology alignment of block copolymers induced by injection molding", Polymer, 2009, vol. 50, p. 5837-5845 (Year: 2009).*

(Continued)

*Primary Examiner* — Gerard Higgins
(74) *Attorney, Agent, or Firm* — Harness, Dickey & Pierce, P.L.C.

(57) ABSTRACT

A heart valve is at least partially constructed from a block-copolymer, the block-copolymer having a phase structure formed by its constituent blocks, and wherein the phase structure is arranged so as to produce anisotropic physical properties in the heart valve.

12 Claims, 9 Drawing Sheets

(51) Int. Cl.
*B29K 96/04* (2006.01)
*B29L 31/00* (2006.01)

(56) References Cited

U.S. PATENT DOCUMENTS

| | | | | |
|---|---|---|---|---|
| 2003/0118800 A1* | 6/2003 | Thomas | ............ | C09D 153/025 428/105 |
| 2005/0098914 A1* | 5/2005 | Varma | .................. | A61L 29/049 264/108 |
| 2006/0241744 A1 | 10/2006 | Beith | | |
| 2009/0117334 A1 | 5/2009 | Sogard et al. | | |
| 2014/0005772 A1 | 1/2014 | Edelman et al. | | |

FOREIGN PATENT DOCUMENTS

| | | |
|---|---|---|
| JP | H10330494 A | 12/1998 |
| JP | H11322964 A | 11/1999 |
| WO | WO-2007104965 A2 | 9/2007 |
| WO | WO-2013-055977 A1 | 4/2013 |

OTHER PUBLICATIONS

Stasiak et al. "Engineering orientation in block copolymers for application to prosthetic heart valves", Func. Mat. Lett., 2010, vol. 3, p. 1-4 (Year: 2010).*

Stasiak et al. "A real time SAXS study of oriented block copolymers during fast cylical deformation, with potential application for prosthetic heart valves", Soft Mater., 2011, vol. 7, p. 11475-11482 (Year: 2011).*

Stasiak, et al.:, "Mechanical strength of sutured block copolymers films for load bearing medical applications," Bio-Medical materials and Engineering 24 (2014), pp. 563-569.

Zaffora, et al., "Design of Biomorphic Polymeric Heart Valve Prosthes by Means of FEM Modeling," Proceedings of the ASME 2010 Summer Bioengineering Conference (SBV2010), Jun. 16-19, 2010, Naples, Florida.

Zaffora, et al.: "Improvement of Static Performances of Biomorphic Polymeric Heart Valve Prostheses by Tailoring the Material Orientation", International Journal of Artificial Organs 34 (2011), Oct. 9-12, 2011, Porto, Portugal, p. 706.

James, Victoria and Ginns, Marcus: "Diffuse interests, Dr. Geoff Moggridge is using his fascination with how substances mix together in diverse and potentially life-changing ways," Cambridge Alumni Magazine, Issue 70, Michaelmas 2013, pp. 28-31.

International Search Report and Written Opinion of the International Searching Authority issued in PCT/GB2015/050346, mailed Aug. 4, 2015; ISA/EP.

Combined Search and Examination Report issued in GB 1403454.0 on Oct. 14, 2014.

* cited by examiner

HEART VALVE

CROSS-REFERENCE TO RELATED APPLICATIONS

This application is a continuation of U.S. patent application Ser. No. 15/122,116 filed on Aug. 26, 2016. This application claims the benefit of U.S. National Phase application under 35 U.S.C. 371 of International Application No. PCT/GB2015/050346, filed on Feb. 9, 2015 and published in English as WO 2015/128605 on Sep. 3, 2015, which is based on and claims the benefit of priority from Great Britain Patent Application No. 1403454.0 filed on Feb. 27, 2014. The entire disclosures of each of these applications are incorporated herein by reference.

FIELD

The present disclosure relates to provision of a prosthetic heart valve made from block copolymers.

BACKGROUND

This section provides background information related to the present disclosure which is not necessarily prior art.

Prosthetic heart valves are commercially available, and broadly fall into two categories: (i) rigid inorganic valves (for example, made from pyrolytic carbon) and (ii) organic valves formed from animal tissue. Both types of valve have different advantages and disadvantages. The inorganic valves, whilst being very durable, increase the risk of blood clotting. In contrast, the inorganic valves have less risk of clotting but have a more limited lifespan, since they are constructed from preserved, dead, tissue. Another disadvantage of tissue-based valves is that they are more easily damaged by, e.g., crimping during the fitting of the valve.

One area of research has considered the use of organic polymers as an alternative material for creating the artificial valves. For example, WO 2013/055977 considers the use of a poly(styrene-isobutylene-styrene) (or SIBS) block copolymer, which was selected for its desirable bulk physical properties.

However, valves made of such materials have been unacceptably susceptible to damage and material fatigue due to the repeated stresses of operation. In particular, the valve leaflets, which operate to open and close the valve, undergo particularly high stresses (i.e. large stress concentration) where they are attached to the supporting structure (which is more rigid), and are prone to failure when made of polymer.

The exploitation of uni-axially aligned phase structures in block copolymers has been considered in Stasiak et al., Functional Materials Letters 3 (2010) 249-251; Zaffora et al., Proceedings of the ASME Summer Bioengineering Conference, Naples, Florida (2010) 187-188; Stasiak et al., Soft Matter 7 (2011) 11475-11482; Zaffora et al., International Journal of Artificial Organs 34 (2011) 706; Stasiak et al., Biomedical Materials and Engineering 24 (2014) 563-569. Whilst these studies show that anisotropic structures and mechanical properties can be of value for application in heart valve leaflets, uni-axial orientation does not accurately mimic the structure in natural tissues and the processing method required makes the development of circumferential orientation very difficult to achieve.

Native aortic heart valves exhibit anisotropic material behaviour which is directly related to its microstructure. The valve leaflet tissue consists of layers exhibiting highly anisotropic arrangements of collagen fibres. The fibrosa and ventricularis layers contain circumferentially oriented fibres, with the function of bearing stress during loading. There is also a layer of elastin present, oriented mainly radially in the ventricularis, and its function is to maintain a specific collagen fibre configuration and to return the fibres to their unloaded state intact when the load has been released.

The mechanical anisotropy of human aortic heart valve leaflets is evident in measured values of the elastic modulus, which is much higher in the circumferential direction (measuring 14.5 MPa) than in the radial direction (1.5 MPa).

EP 2,208,518 discusses injection moulding of block-copolymers in the presence of lubricants and other components.

SUMMARY

This section provides a general summary of the disclosure, and is not a comprehensive disclosure of its full scope or all of its features.

The present invention aims to provide improved heart valve prostheses by meeting and maintain the demanding functional mechanical requirements, by more closely mimicking the structure of native valves.

According to a first aspect of the present invention there is provided a heart valve, at least partially constructed from a block-copolymer, the block-copolymer having a phase structure formed by its constituent blocks, and wherein the phase structure is arranged so as to produce anisotropic physical properties on a macroscopic scale in the heart valve. The anisotropic macroscopic properties of the block copolymer material result in a heart valve that behaves more like a natural valve. Further, the anisotropic properties can be exploited to extend the life expectancy of the valve by reducing the stress concentration experienced by the valve.

Preferably, the heart valve comprises leaflets for actuating the valve, and the leaflets are made from the block-copolymer with the arranged phase structure. As such, the leaflets have anisotropic physical properties.

Preferably, the block copolymer forms a phase structure comprising cylinders of a first polymer material in a matrix of another polymer material, and the first polymer material is a glassy polymer at body temperature and the second polymer material is a rubbery polymer at body temperature. As such, the block copolymer behaves like a composite material, with stiffening rods in a stretchier matrix.

The block-copolymer can be one of SIBS30 (poly(styrene-block-isobutylene-block-styrene), 30% styrene); SIS30 (poly(styrene-block-isoprene-block-styrene), 30% styrene); SI/BS19 (poly(styrene-block-isoprene/butadiene-block-styrene), 19% styrene); SIS18 (poly(styrene-block-isoprene-block-styrene), 18% styrene); SE/BS30 (poly(styrene-block-ethylene/butylene-block-styrene), 30% styrene); SE/BS20 (poly(styrene-block-ethylene/butylene-block-styrene), 20% styrene); SE/PS20 (poly(styrene-block-ethylene/propylene-block-styrene), 20% styrene); and SE/PS22 (poly(styrene-block-ethylene/propylene-block-styrene), 22% styrene).

The phase structure is preferably arranged to produce layers in which the phase structure is differently aligned in neighbouring layers. At certain points the alignment in neighbouring layers may be the same, but at others the alignment can be substantially different. The layers can include two outer layers in which the phase structure is aligned substantially perpendicularly to the phase structure within the inner layer. Such a phase structure is obtainable by injection moulding, and mimics the tissue structure in a natural heart valve.

The total thickness of the two outer layers can be from 25% to 75% of the thickness of the heart valve. Optionally, the total thickness can be around 50%.

According to another aspect, the invention provides a method of manufacturing a heart valve, the method comprising: a step of injection moulding at least one part of the heart valve from a block-copolymer, wherein the injection moulding is performed at a temperature below the order-disorder transition temperature for the block copolymer, such that a phase structure is present in the molten block-copolymer; a step of cooling the at least one part of the heart valve after it is moulded, without heating the at least one part above the order-disorder transition temperature between the step of injection moulding and the step of cooling, so as to preserve an arrangement of the phase structure created during the step of injection moulding and produce anisotropic physical properties in the heart valve.

The step of injection moulding includes the use of a mould with injection moulding points positioned at the top and/or base of one or more leaflets of the heart valve.

According to another aspect of the invention, there is provided a method of designing a mould for injection moulding a heart valve from block copolymer below the block copolymer's order-disorder transition temperature, the method comprising: modelling at least a section of a heart valve produced by the mould, including modelling the stress concentration in the valve and accounting for the orientation of the phase structures within the block copolymer; changing the injection position of the block copolymer in the model of the mould, and remodelling the at least a section of the heart valve; selecting an injection position, based on the modelling and remodelling, that provides the least stress concentration in the valve; and producing a mould with the injection position in the position that provides the least stress concentration in the valve. Accordingly, the best performing valve can be identified and produced for a particular valve shape and set of processing conditions.

According to another aspect, there is provided a method of producing anisotropic physical properties in a solid block copolymer, the method comprising: a step of injection moulding the block-copolymer at a temperature below the order-disorder transition temperature for the block copolymer, such that a phase structure is present in the molten block-copolymer; a step of cooling the at least one part of the heart valve after it is moulded, without heating the at least one part above the order-disorder transition temperature between the step of injection moulding and the step of cooling, so as to preserve an arrangement of the phase structure created during the step of injection moulding and to produce anisotropic physical properties in the heart valve.

According to another aspect, there is provided a solid block copolymer material, the block-copolymer having a phase structure formed by its constituent blocks, wherein the phase structure is arranged to produce layers in which the phase structure is differently aligned in neighbouring layers. A medical prosthetic, can at least partially comprise a solid block copolymer material of this type. Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is a diagram depicting the geometry for injection moulding a block copolymer sample and subsequently x-raying it;

FIG. 2, view a, is 2D SAXS intensity pattern for an injection moulded block copolymer material;

FIG. 2, view b, is an azimuthal integration of the 2D SAXS data corresponding to FIG. 2, view a;

FIG. 3, view a, is an azimuthal intensity profile for a full X-axis scan of a sample of a particular thickness;

FIG. 3, view b, is an azimuthal intensity profile for a full X-axis scan of a sample of another thickness;

FIG. 3, view c, is an azimuthal intensity profile for a full X-axis scan of a sample of yet another thicknesses;

FIG. 3, view d, is an azimuthal intensity profile for a full Y-axis scan of a sample of a particular thickness;

FIG. 3, view e, is an azimuthal intensity profile for a full Y-axis scan of a sample of another thickness;

FIG. 3, view f, is an azimuthal intensity profile for a full Y-axis scan of a sample of yet another thickness;

FIG. 4, view a, is a vector plot representing orientation along X and Y axes for the sample in FIG. 3, view a;

FIG. 4, view b, is a vector plot representing orientation along X and Y axes for the sample in FIG. 3, view b;

FIG. 4, view c, is a vector plot representing orientation along X and Y axes for the sample in FIG. 3, view c;

FIG. 4, view d, is a vector plot representing orientation along X and Y axes for the sample in FIG. 3, view d;

FIG. 4, view e, is a vector plot representing orientation along X and Y axes for the sample in FIG. 3, view e;

FIG. 4 view f, is a vector plot representing orientation along X and Y axes for the sample in FIG. 3, view f;

Figure 9:
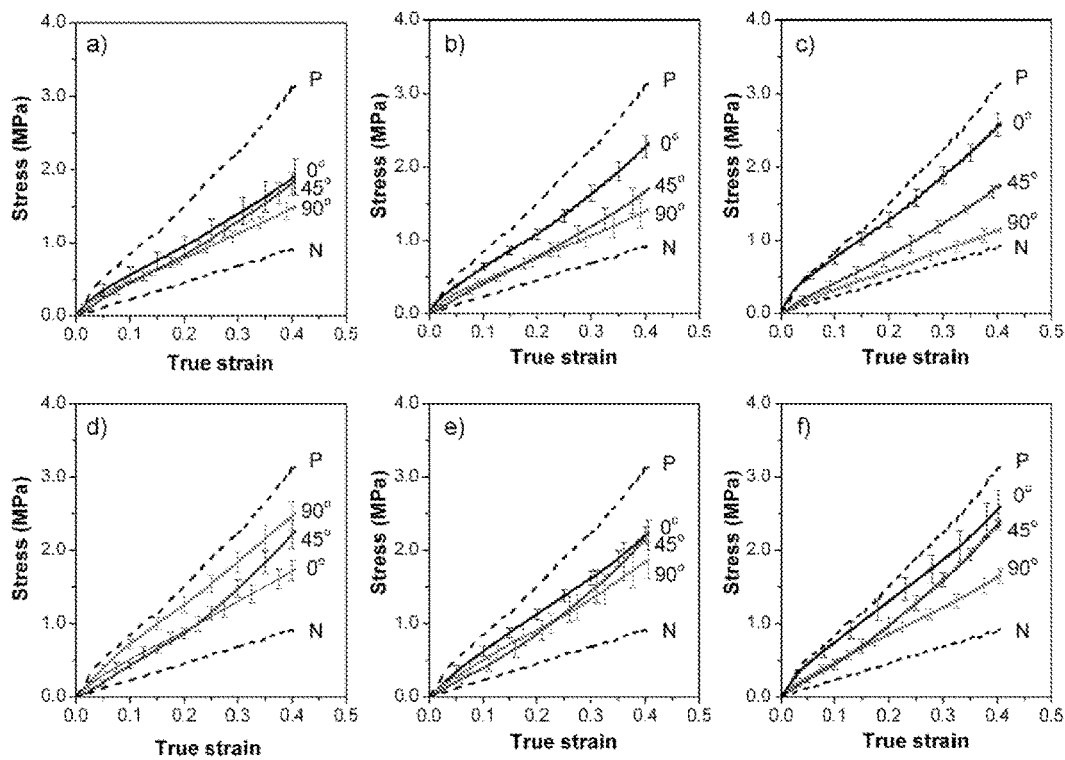
Figure 10:
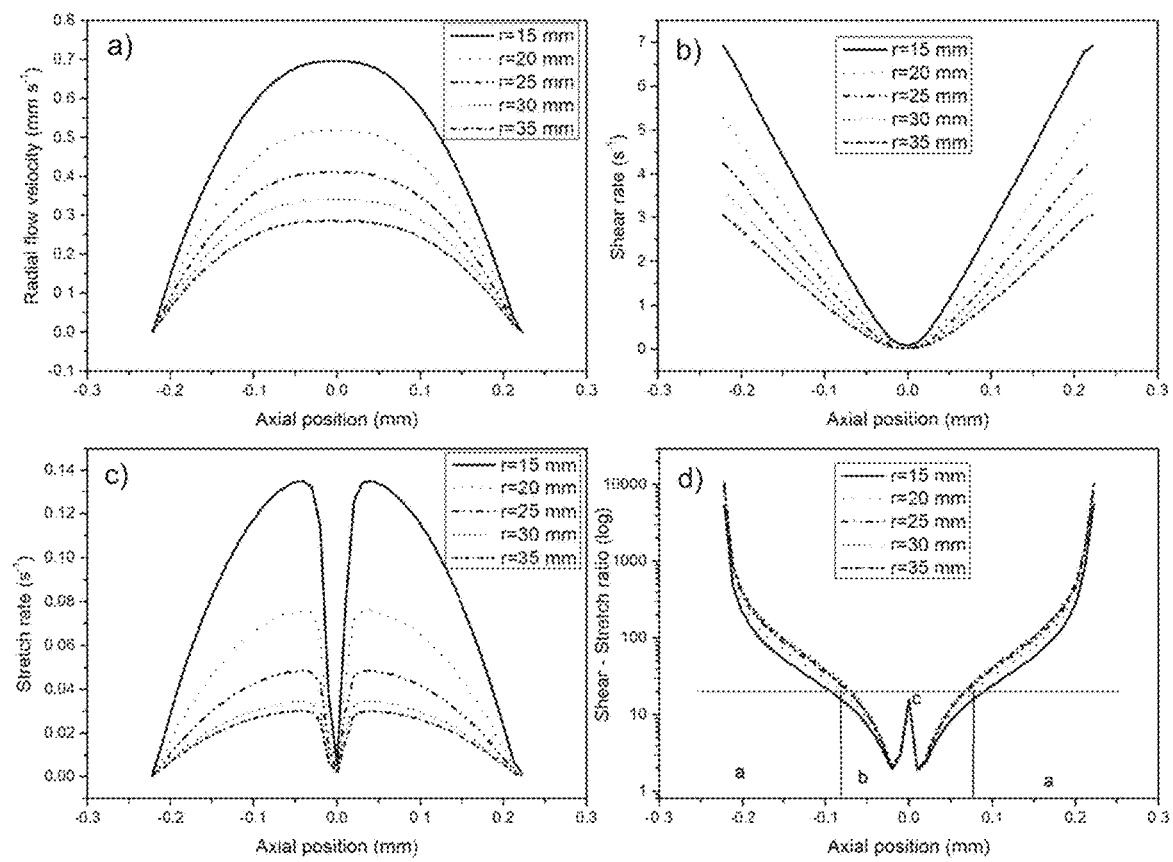
Figure 11:
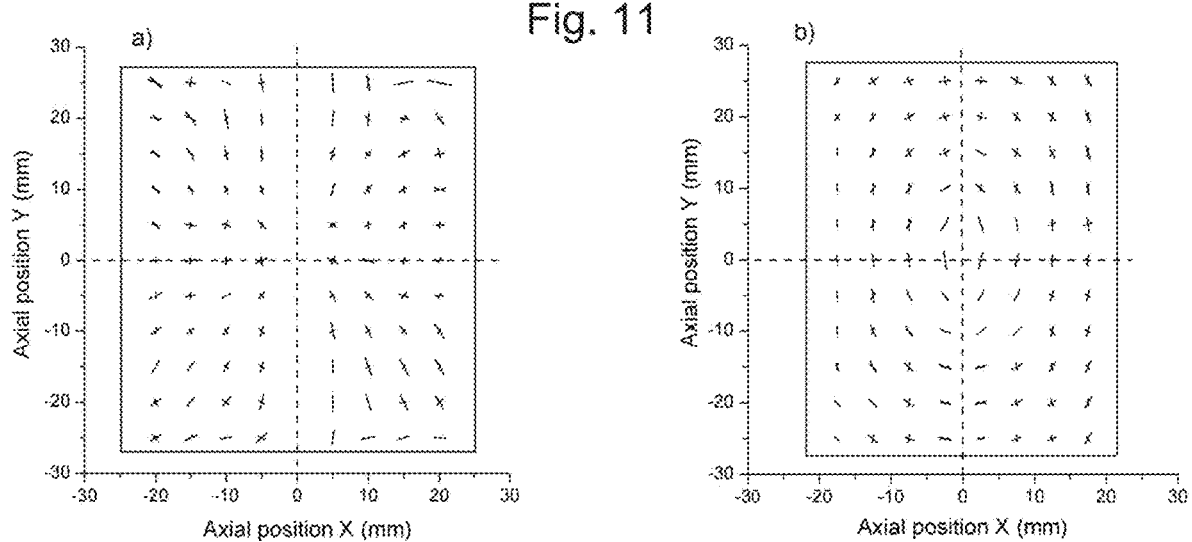
Figure 12:
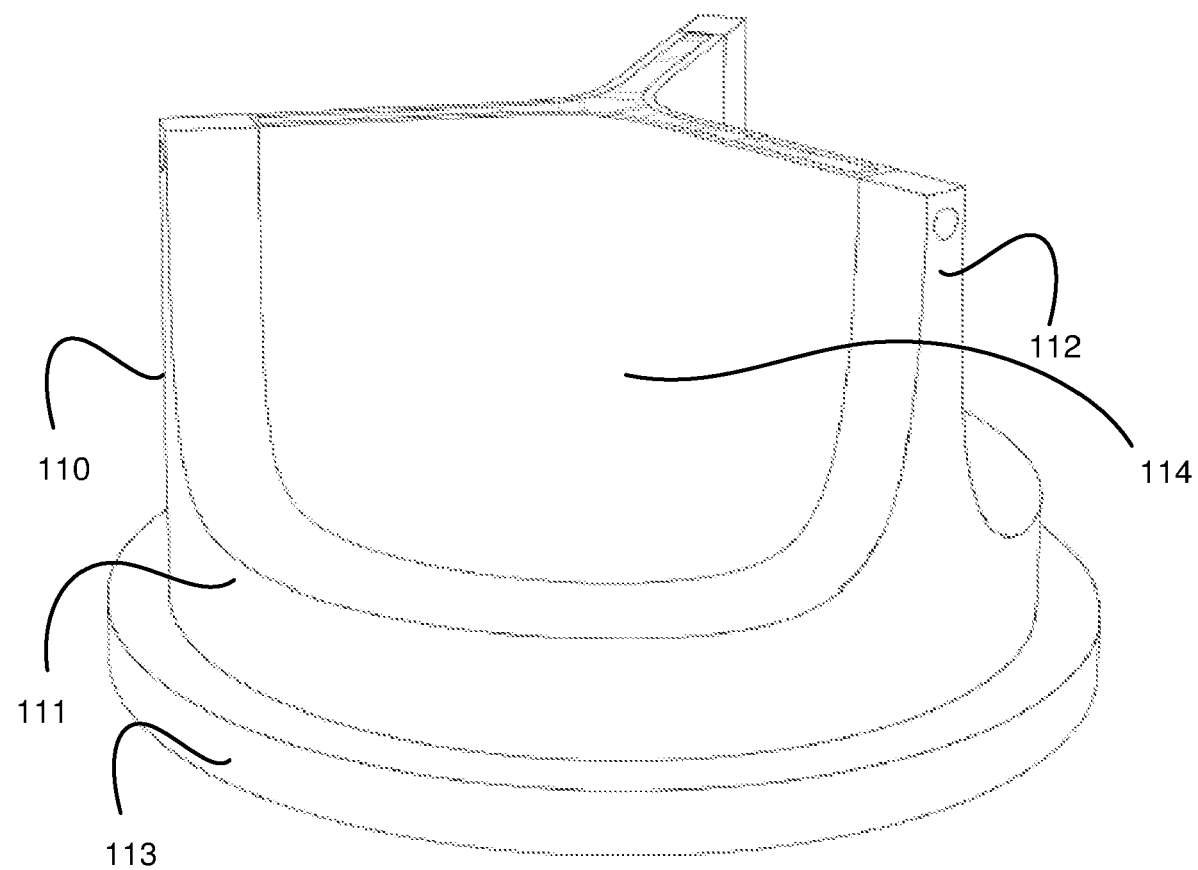
Figure 13A:
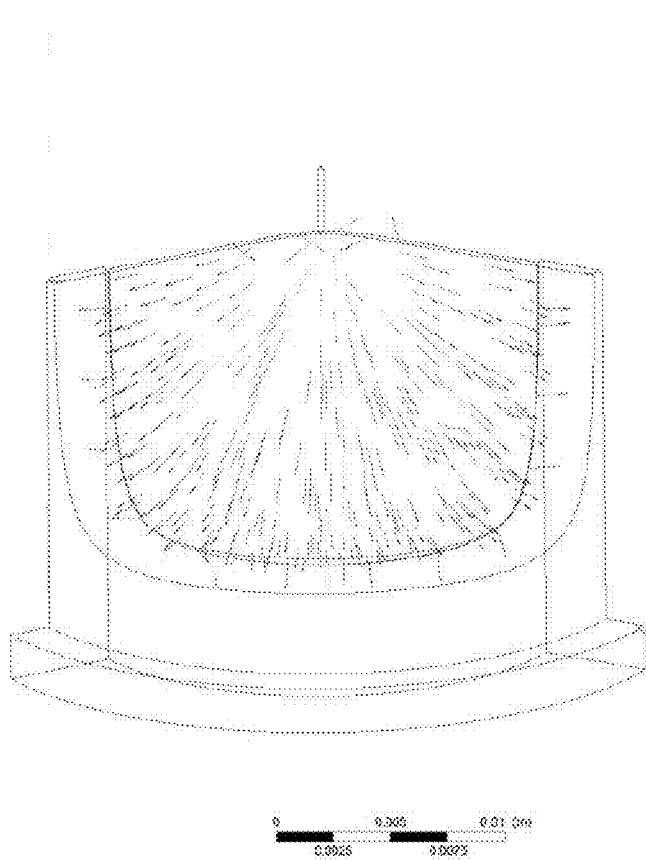
Figure 13B:
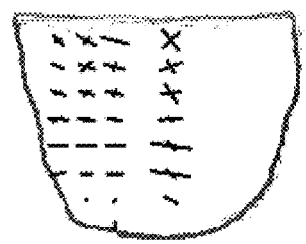
Figure 13C:
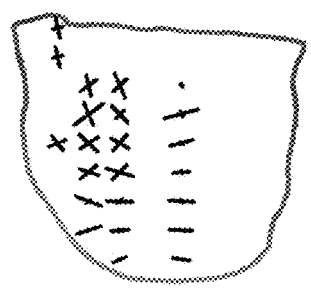
Figure 13D:
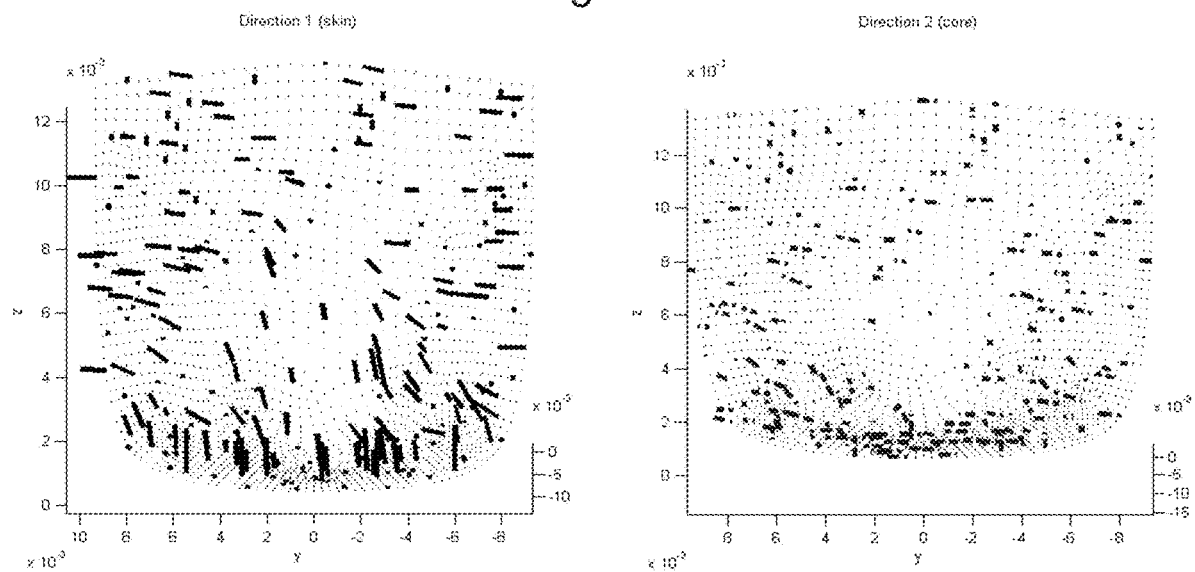
Figure 14A:
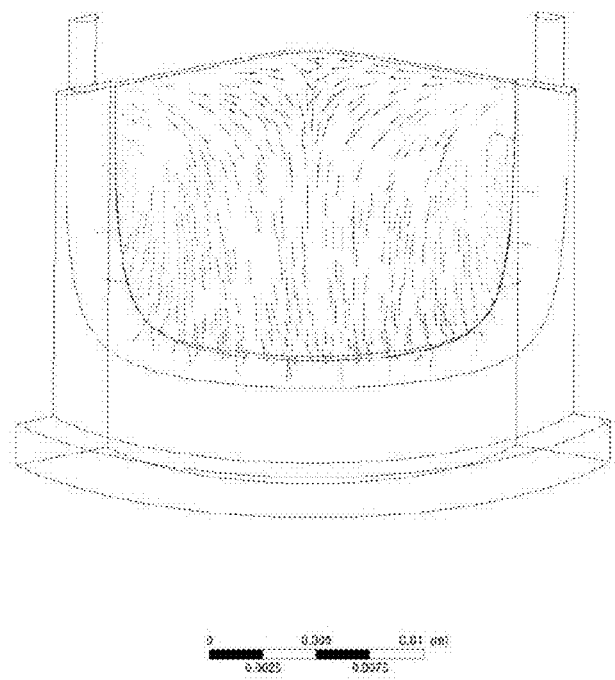
Figure 14B:
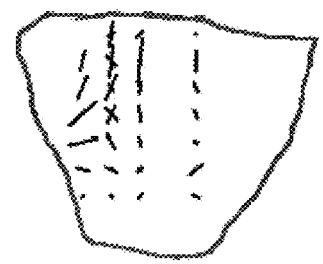
Figure 14C:
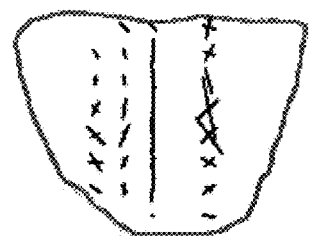
Figure 14D:
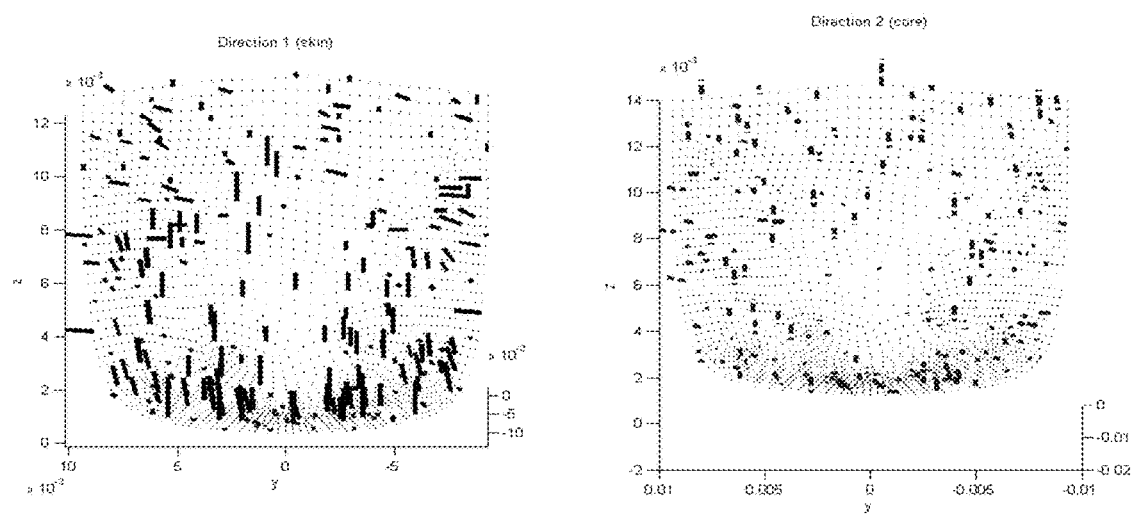
Figure 15A:
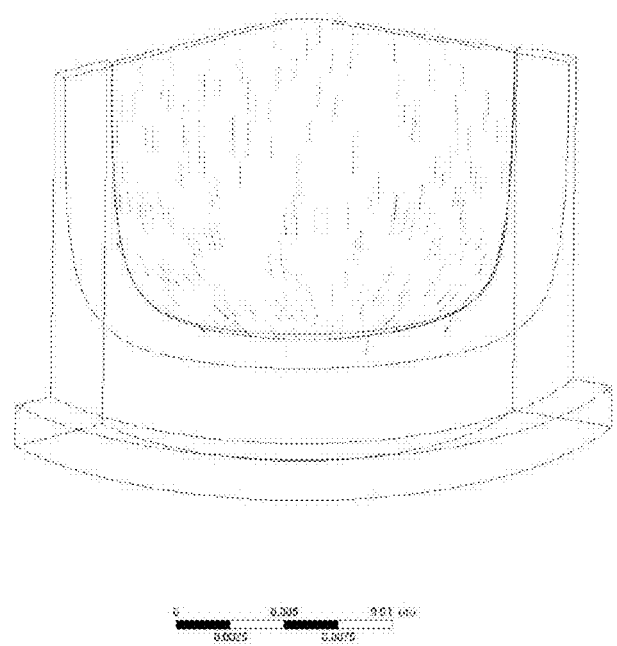
Figure 15B:
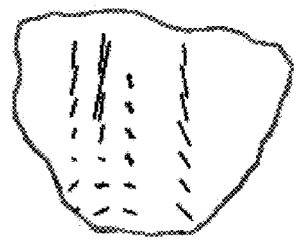
Figure 15C:
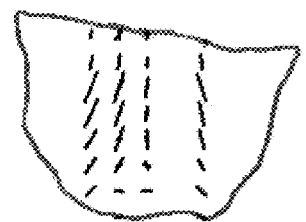
Figure 15D:
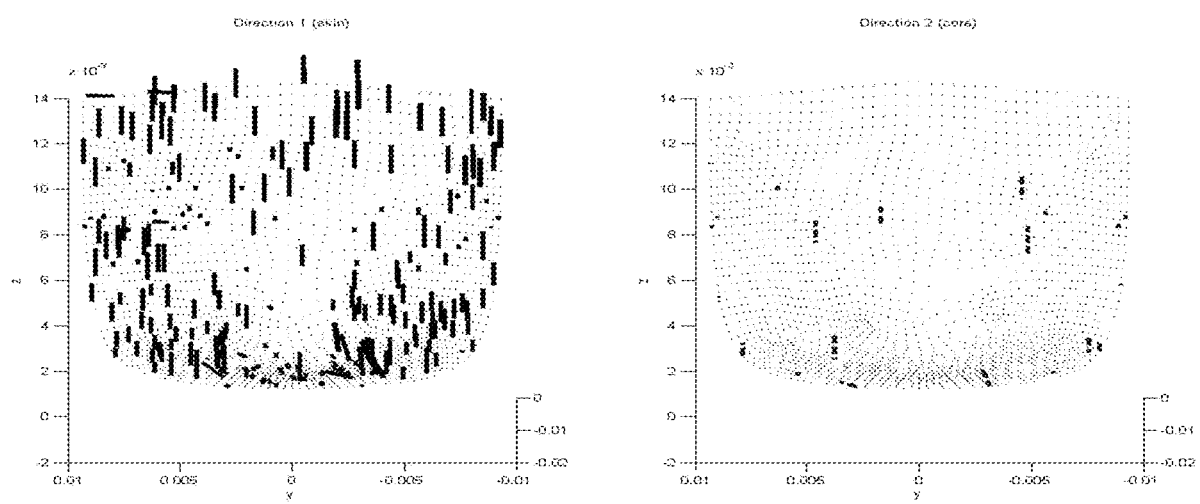

FIG. 9, view a, shows the result of tensile testing for a sample thicknesses and injection rate;

FIG. 9, view b, shows the result of tensile testing for a sample thicknesses and injection rate;

FIG. 9, view c, shows the result of tensile testing for a sample thicknesses and injection rate;

FIG. 9, view d, shows the result of tensile testing for a sample thicknesses and injection rate;

FIG. 9, view e, shows the result of tensile testing for a sample thicknesses and injection rate;

FIG. 9, view f, shows the result of tensile testing for a sample thicknesses and injection rate;

FIG. 10, view a, is a graph of the modelled velocity profile for injection moulded block copolymer between thin plates;

FIG. 10, view b, is the shear rates graph corresponding to FIG. 10, view a;

FIG. 10, view c, shows the stretch rates corresponding to FIG. 10, view a;

FIG. 10, view d, shows the ratio of stretch rate to shear rate corresponding to FIG. 10, view a;

FIG. 11, view a, is a map of orientation within injection moulded SI-BS19;

FIG. 11, view b, is a map of orientation within injection moulded SIBS30;

FIG. 12 is a schematic representation of an injection moulded heart valve;

FIG. 13 A is a diagram comparing a calculated injection profile using an injection geometry;

FIG. 13 B is a diagram comparing an experimentally determined orientation following injection moulding into a heart valve geometry using an injection geometry;

FIG. 13 C is a diagram comparing an experimentally determined orientation following injection moulding into a heart valve geometry using an injection geometry;

FIG. 13 D is a diagram comparing a modelled orientation;

FIG. 14 A is a diagram comparing a calculated injection profile using an injection geometry;

FIG. 14 B is a diagram comparing an experimentally determined orientation following injection moulding into a heart valve geometry using an injection geometry;

FIG. 14 C is a diagram comparing an experimentally determined orientation following injection moulding into a heart valve geometry using an injection geometry;

FIG. 14 D is a diagram comparing a modelled orientation;

FIG. 15 A is a diagram comparing a calculated injection profile using an injection geometry;

FIG. 15 B is a diagram comparing an experimentally determined orientation following injection moulding into a heart valve geometry using an injection geometry;

FIG. 15 C is a diagram comparing an experimentally determined orientation following injection moulding into a heart valve geometry using an injection geometry; and FIG. 15 D is a diagram comparing a modelled orientation.

Corresponding reference numerals indicate corresponding parts throughout the several views of the drawings.

DETAILED DESCRIPTION

Example embodiments will now be described more fully with reference to the accompanying drawings.

The present invention aims to produce an improved heart valve, by producing a valve which more closely mimics the structure of a native valve. This is achieved by making use of the property of block copolymers (BCPs) to self assemble into different phase structures. Although BCPs have been considered for use in heart valves before, such consideration has focussed upon their bulk physical properties.

BCPs are a class of polymers that form nano-scale morphologies, due to the presence of 'blocks' of different repeated monomers within the same polymer chain. Below the order-disorder transition (ODT) temperature, the different blocks separate into different phases, but are constrained by bonds within the polymer chains. As a result, different phase structures are produced, depending upon the number of phases present and the relevant volume fractions. Above the ODT temperature, the different phases mix, and no phase structures are seen.

For a two-phase system, approximately equal volume fractions for the two phases will result in a lamellar morphology (i.e. sheets of one phase separated by sheets of the other), whilst reducing the volume fraction of one phase will result (in order of decreasing volume fraction) in the so-called 'gyroid' structure, then cylinders and then spheres of the minor phase in a matrix of the other. As such, it is conventional to specify BCP composition in terms of volume fractions or percentages, and all BCP compositions below are provided as volume fractions or percentages, unless specified otherwise.

The bulk physical properties of BCPs often depend critically on the phase orientation induced during processing, although this orientation requires the processing of the BCP below the ODT temperature.

A BCP processed above the ODT temperature will not develop any phase structure, and if cooled in a quiescent state will develop randomly oriented micro-domains of phase structures equivalent to a polycrystalline structure. In contrast, for example, in thermoplastic elastomers with a cylindrical morphology processed below the ODT, the alignment of the cylindrical phase structures results in orthotropic mechanical properties.

As such, where BCPs are selected for use due to their generic bulk properties (e.g. in WO 2013/055977) and isotropic properties are desired, no effort is made to orient or align the nanophases, resulting in the aforesaid polycrystalline structure with micro-regions of alignment in different directions (or, as in WO 2013/055977, in which the polymer is heated and then cross-linked, the nanophases can be destroyed and prevented from re-forming at all).

Cylinder-forming block copolymers have been known to orient strongly in the direction of flow when confined to a channel e.g. in a channel die or during extrusion. This results in strongly anisotropic mechanical properties, with (for the case of styrenic cylinders in a rubbery matrix) a higher Young's modulus in the direction of orientation of the cylinders.

The inventors have shown that such behaviour can be extended to flow in two dimensions, by compression moulding between two parallel plates; the result is radially oriented cylindrical phase structures. It is therefore commonly assumed that orientation of anisotropic particles is governed by flow direction: thus when filling a mould one expects flow path induced alignment.

However the inventors have unexpectedly found a different type of orientation, during morphological investigations of injection moulded films of poly(styrene-block-isoprene-block-styrene) containing 30% wt styrene (SIS30), a block copolymer with cylindrical morphology. Anisotropic domains forming a layered structure, exhibiting bi-directional orientation, are observed in this scenario.

Using synchrotron X-ray diffraction, a detailed microstructural analysis uncovers distinct layers of orthogonal orientation at the skin and core of the samples. The bi-directional alignment is stable, extending throughout the sample. This complex micro-domain orientation can be explained by the balance of shear flow and extensional flow in different regions of the sample during the injection moulding process.

Such a layered structure with bi-directional orientation has not previously been reported in a solid material. However, such a material with a bi-directional microstructure, which is preserved upon solidification, more closely mimics the structure of a native heart leaflet and so is a desirable material for forming a prosthetic heart valve. Indeed, by linking the morphology to mechanical properties of the final solid material, a more refined approach to the fabrication of prosthetic heart valve leaflets, in particular, can be taken. Numerical modelling results has shown that even a small amount of orthotropy in the prosthetic material can significantly improve the mechanical behaviour of the valve, and that an appropriate orientation of the fibres can contribute to optimizing the stress distribution in the leaflets.

The description below first considers the generation of the advantageous structure, before considering the application of such structure to a heart valve.

Production of Bi-Directional Alignment

Materials

The discussion below focuses on the block copolymer poly(styrene-block-isoprene-block-styrene) containing 30% wt styrene, commercial name D1164P manufactured by Kraton Polymers, referred to as SIS30. Poly (styrene-block-isoprene-butadiene-block-styrene) having 19% wt styrene (SI-BS19; commercial name D1171P manufactured by Kraton Polymers). Poly(styrene-block-isobutylene-block-styrene) with 30% wt styrene (SIBS30; manufactured by Innovia LLC) is also referred to in FIG. 11.

Injection Moulding

Injection moulding was performed at 160° C., the ODT temperature being in excess of 20° C. for SIS30, via a 1 mm diameter inlet pipe into the centre of two parallel circular plates of diameter 80 mm. Two volumetric injection rates and three sample thicknesses were tested, as shown in Table 1.

TABLE 1

Volumetric injection rates and sample thicknesses tested

| Injection rate, m$^3$s$^{-1}$ | Sample thickness, mm |
|---|---|
| 7 × 10$^{-8}$ | 0.95 ± 0.05 |
|  | 0.45 ± 0.02 |
|  | 0.23 ± 0.03 |
| 2 × 10$^{-8}$ | 0.97 ± 0.05 |
|  | 0.44 ± 0.02 |
|  | 0.30 ± 0.02 |

X-Ray Analysis

Synchrotron Small Angle X-ray Scattering (SAXS) was performed on beamline I22 at Diamond Light Source, Harwell Science and Innovation Campus, UK. The energy used was 12.4 keV with a 6 m camera length and beamstop in the middle of the RAPID 2D detector. Further details of the beam line setup and technical characteristics can be found elsewhere http://www.diamond.ac.uk/Home/Beamlines/I22). For quantitative analysis of the radial and circumferential orientation only the X-ray frames showing fully developed orientation, no closer than 15 mm from the injection point, were considered for the calculations. It was found that there were up to 10% variations in the characteristic d-spacing measured at various positions of the sample, for both radial and circumferential orientations. This indicates that individual elements of the fluid deformed during moulding and froze in a locally pre-strained state. Peak broadening by strain resulted in larger integrated intensities, not representative of the amounts present. Therefore a correction based on previously described stress-intensity relations for SIS30 has been applied (ref—Stasiak et al. (2011) Soft Matter 7, 11475-11482).

Modelling

Numerical modelling of the system was carried out using ANSYS Polyflow. We assumed incompressible, steady, continuous, axisymmetric flow, with a purely viscous, 3-dimensional and isotropic medium. A no-slip condition was assumed at the interfaces with the upper and lower plates and the inlet wall. The plates were meshed with a radial resolution of 0.5 mm and axial resolution of 100 divisions between plates. The viscosity of the polymer was described by the Carreau-Yasuda equation, parameters (given below) being determined by rheometry experiments on the material (ARES parallel plate rheometer).

Rheological properties of SIS30 used in the Carreau-Yasuda equation:

| $\eta_\infty$ | 5.16e3 Pa s | Infinite shear viscosity |
| $\eta_0$ | 1.62e5 Pa s | Zero shear viscosity |
| $\lambda$ | 66 Pa s$^{-1}$ | Critical shear rate at which viscosity decreases |
| a | 1.636 | Width of transition region between zero shear and power law |
| n | 0.145 | Power law region exponent |

Shear rate and stretch rate was derived from the deformation tensor, D.

$$\varepsilon' = 6III_D/II_D = 6(\det D)/(tr\ D \cdot D)$$

where $II_D$ and $III_D$ are the $2^{nd}$ and $3^{rd}$ invariants of the deformation tensor, tr is the trace, and det is the determinant.

Discussion

Figure 1:
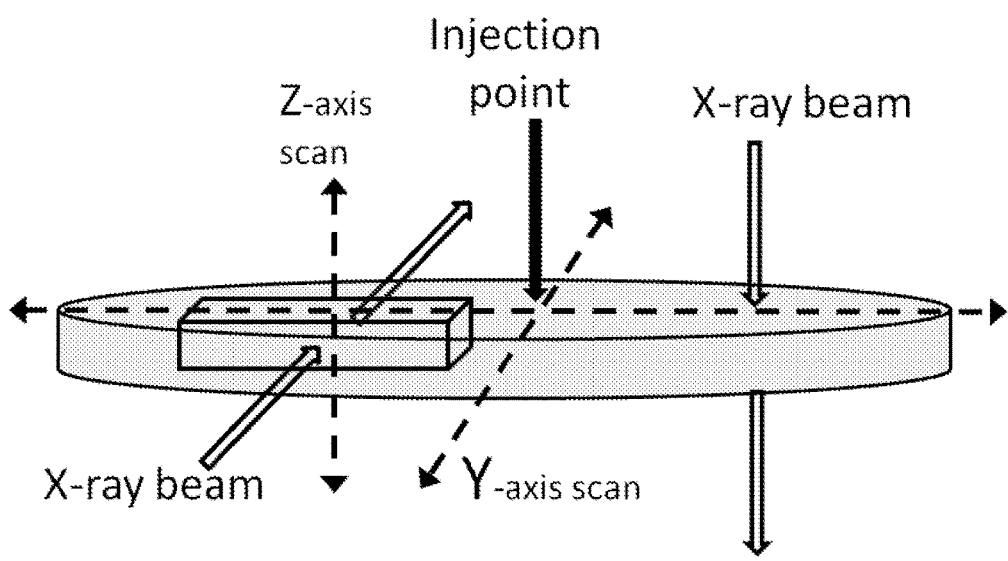

Samples were injection moulded into discs of diameter 80 mm. The injection point was located in the centre of the top plate and the polymer melt was injected at 160° C., as shown in FIG. 1. FIG. 1 shows the sample geometry, with two paths for the 2D Small Angle X-ray Scattering (SAXS) measurements and x-ray beam positions. Two injection rates and three sample thicknesses were used, as set out above. The oriented structure induced by processing was preserved by rapid cooling of the mould—the temperature dropped from 160° C. to 40° C. in approximately one minute.

Microstructure orientation was measured by SAXS performed at the Diamond Light Source, Oxfordshire, UK. To map the orientation distribution within the material, samples were X-ray scanned along X, Y and Z axis as shown in FIG. 1. The spatial resolution of collected SAXS frames was 1 mm for X and Y scans and 0.05 mm or 0.1 mm for Z axis scans.

FIG. 2a shows a representative experimental scattering pattern (for the 0.95 mm thick sample with an injection rate of 7×10$^{-8}$ m$^3$s$^{-1}$) as scanned along the X axis depicted in FIG. 1 (lighter colours showing greater intensity of scattering). The area of azimuthal integration is indicated in FIG. 2a by angle $\chi$, and the integrated azimuthal intensity profile is shown in FIG. 2b.

If the cylindrical phase structures in the block copolymer had been oriented along the flow direction (as would have been expected based on previous experience), then the X-ray scattering images would show two reflections parallel to the flow direction (equatorial spots in FIG. 2), arising from the circumferential d-periodicity (26 nm) of the styrenic cylinders.

Figure 2:
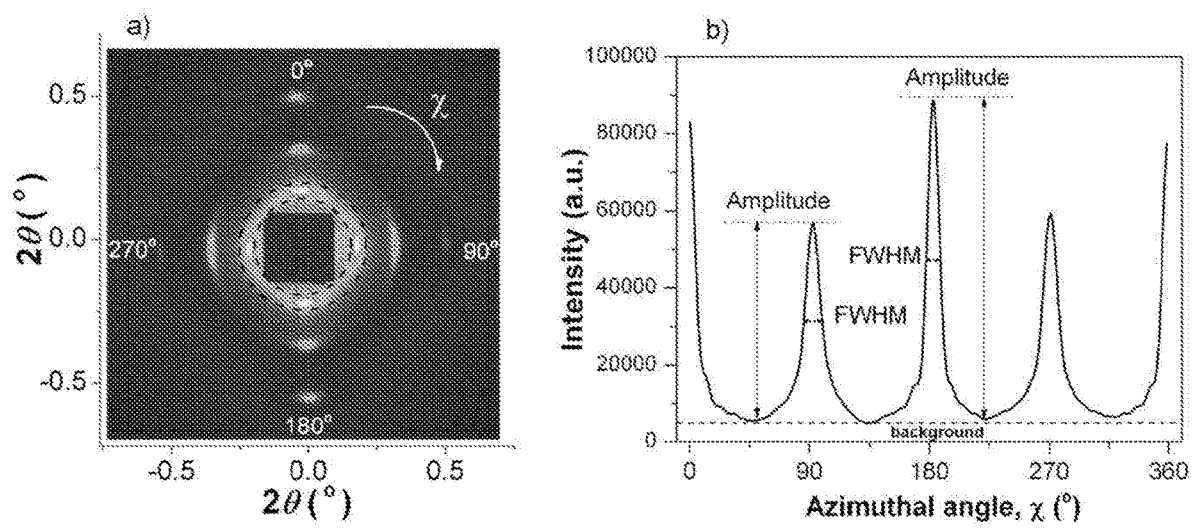

However, as evident from FIG. 2, more complex scattering patterns are observed. The SAXS image (FIG. 2a), contains a pair of equatorial reflections coexisting with another pair of meridional reflections. Both pairs of reflections corresponded to a d-spacing of 26 nm. The SAXS data have been analyzed by azimuthal integration, as shown in FIG. 2a for $\chi$=0-360 degrees. The corresponding intensity profile in FIG. 2b shows four maxima at 0°, 90°, 180° and 270°, indicating alignment along both of the two orthogonal X and Y directions. This demonstrates the presence of a bi-directional orientation of the cylindrical phase structures, in which some of the material is aligned along the flow direction and the rest perpendicular to the flow direction. That is, peaks at 0° and 180° are from radially oriented cylinders; those at 90° and 270° are from circumferentially oriented cylinders.

Figure 3:
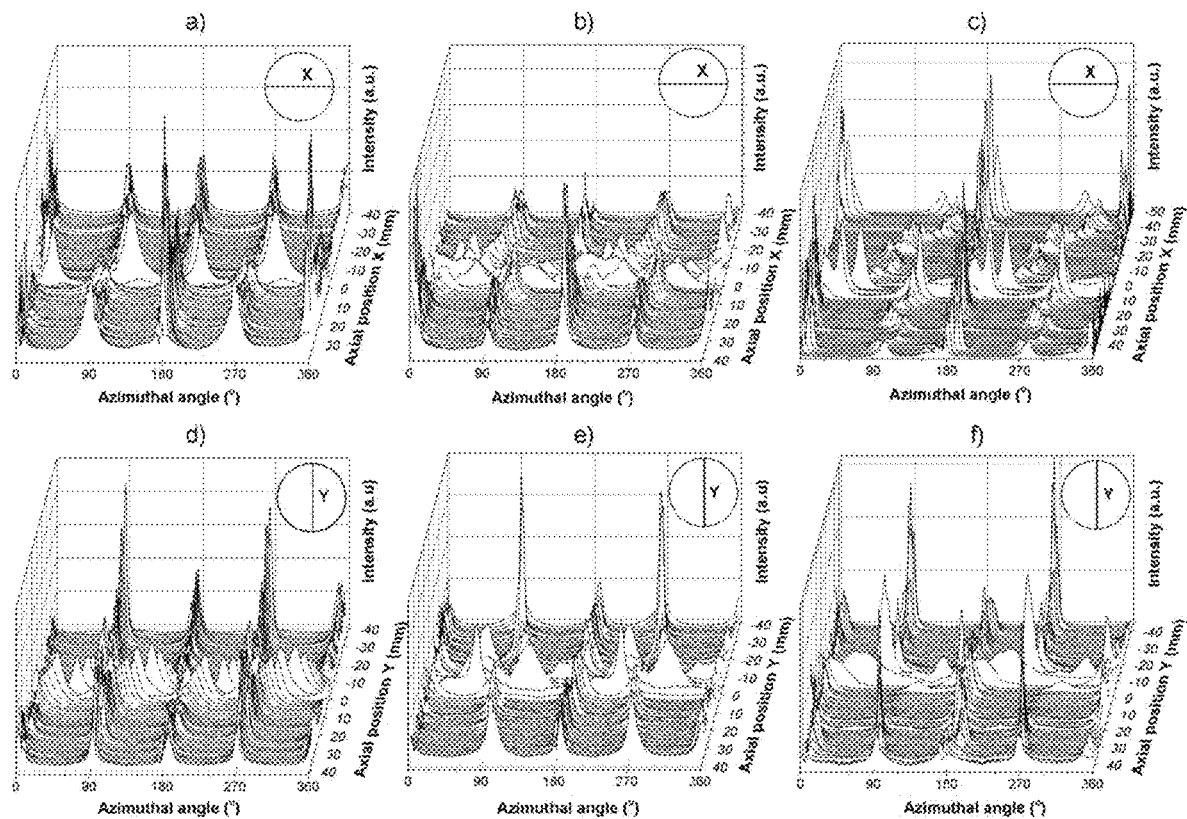

Integrated azimuthal intensity profiles for full X-axis and Y-axis scans are provided in FIG. 3 at three sample thicknesses: (a, d) 0.95 mm, (b, e) 0.45 mm, and (c, f) 0.23 mm. The injection point is at '0' axial position, and the injection rate in all cases was 7×10$^{-8}$ m$^3$s$^{-1}$. Bi-directional orientation is evident across the entire sample (over the whole range of X- and Y-scans) and for all three sample thicknesses.

Azimuthal peak broadening at full width half maximum (FWHM$_{azimuthal}$) was determined as a measure of the degree of anisotropy for the two reflections at 90° and 180°.

Figure 4:
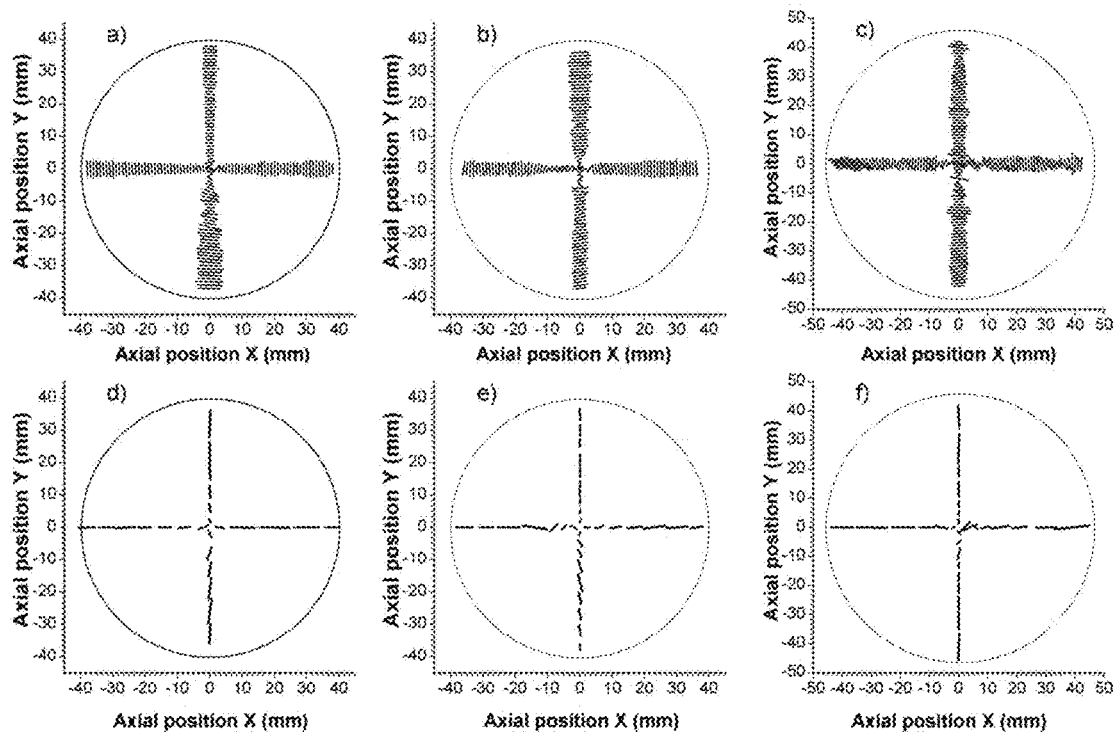

Orientation angle for circumferential (FIGS. 4a-c) and for radial (FIGS. 4d-f) alignment is represented in FIG. 4 as the angle of vector, while the vector's length is proportional to the reciprocal FWHM$_{azimuthal}$ for the relevant reflections. The vector plots in FIG. 4 represent molecular orientation along X and Y axes for various sample thicknesses: (a, d) 0.95 mm, (b, e) 0.45 mm, (c, f) 0.23 mm, all at an injection rate of $7 \times 10^{-8}$ m$^3$s$^{-1}$.

Significant intensity between the peaks at 90° and 180° was observed only in the close vicinity (10 mm or less for all sample thicknesses) of the injection point, associated with flow development after transition from the injection nozzle geometry to the mould. At larger radii, the degree of orientation in the radial and circumferential directions was high throughout the sample.

Figure 5:
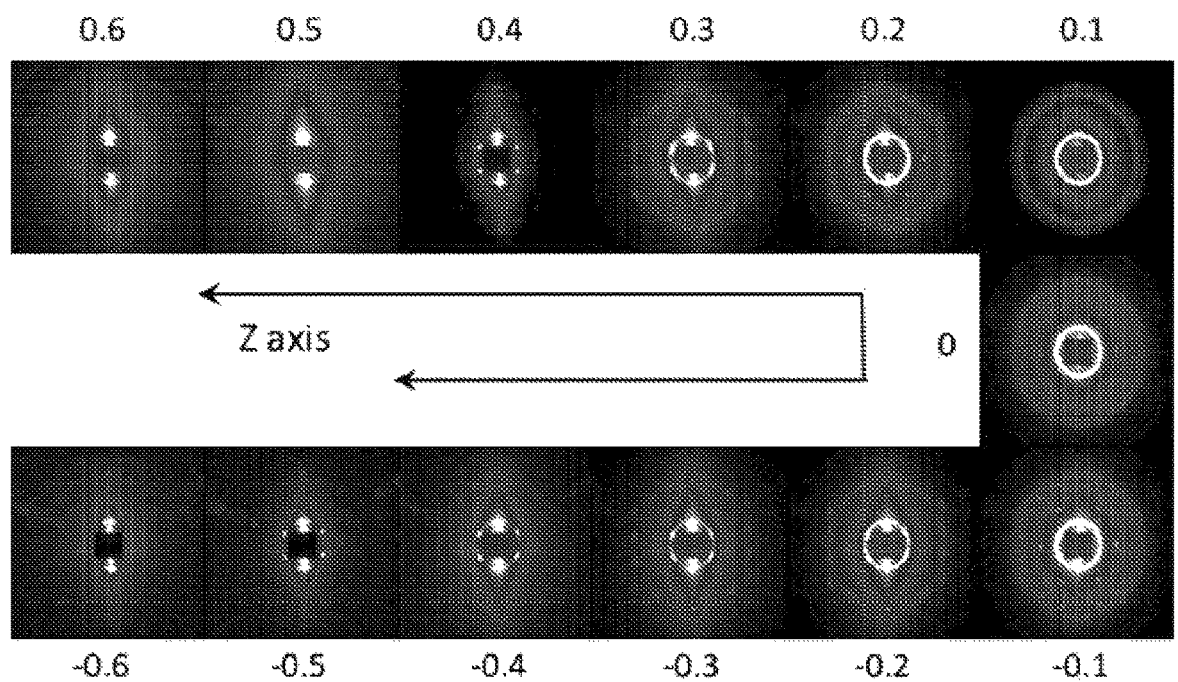
FIG. 5 is a series of 2D SAXs intensity patterns at different positions on the Z axis for a particular block copolymer sample.
Figure 6:
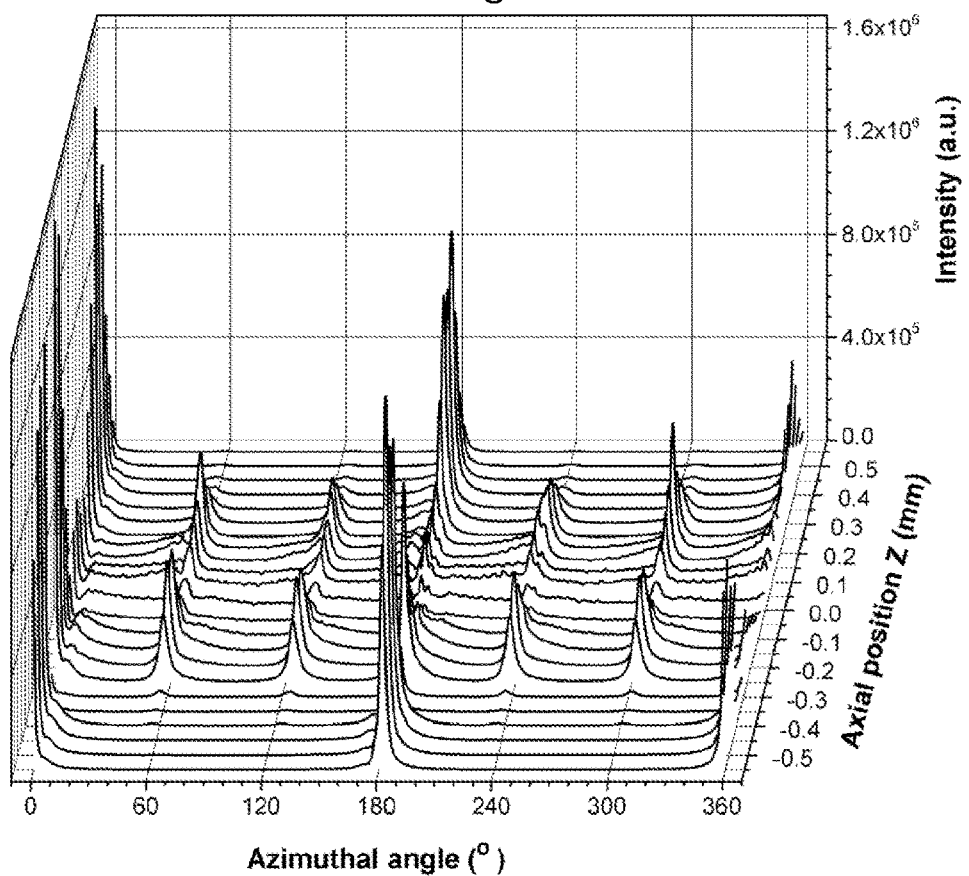
FIG. 6 is a series of azimuthal integrations corresponding to the 2D SAXS intensity patterns in FIG. 5.

A thin radial strip of the 0.95 mm thick sample, cut along the X-direction of the sample, was looked at in cross-section by performing a Z-axis SAXS scan. Representative X-ray images taken at incremental Z positions are shown in FIG. 5 (individual images showing Z axis position in mm, brighter colours indicating greater intensity). FIG. 6 shows azimuthal intensity profiles corresponding to the images in FIG. 5.

At the top of the sample (e.g. Z axis position 0.6) the images show two vertical reflections, indicating radial alignment (parallel to the flow direction) of the microstructure.

Moving deeper into the sample the X-ray image changed to a hexagonal pattern, indicative of close packed cylinders oriented circumferentially (perpendicularly to the flow direction). A fully developed hexagonal pattern is observed, consistent with an almost crystalline degree of organisation of the cylinders, at Z=0.2-0.4 mm in FIG. 5.

The middle zone (around 0.2 mm either side of Z=0 in FIG. 5) contains an area in which the hexagonal spots of the layer just described are blurred into diffraction rings. This indicates that the cylinders are again oriented circumferentially and with a close packed hexagonal structure. However, in this region micro-domains exist which are rotated relative to each other along an axis parallel to the cylinders.

The X-ray scattering observed below Z=0 is symmetric to that above Z=0, as expected.

As the sample was relatively thin compared to the size of the X-ray beam (250 µm vertical dimension and 300 µm horizontal dimension) the collected images represent the sum of morphological features present within the exposure area. As a consequence, in some images two vertical reflections characteristic of radial alignment overlay the hexagonal pattern representing the circumferential orientation; and in others the hexagonal pattern overlays the pattern consisting of diffraction rings.

Figure 7:
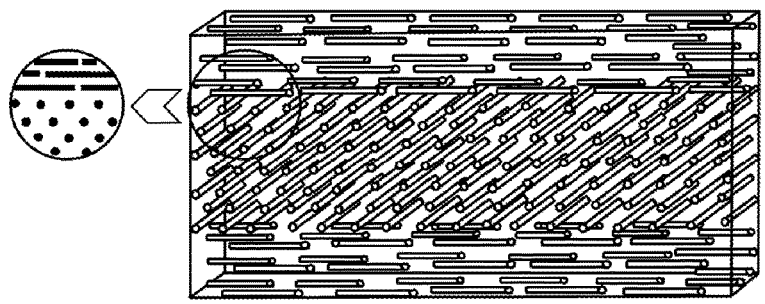
FIG. 7 is a schematic drawing showing the derived arrangement of nanophases in the block copolymer samples.

From the SAXS data, it can be inferred that the injection moulded material shows orthogonally aligned skin and core layers, as sketched schematically in FIG. 7.

Figure 8:
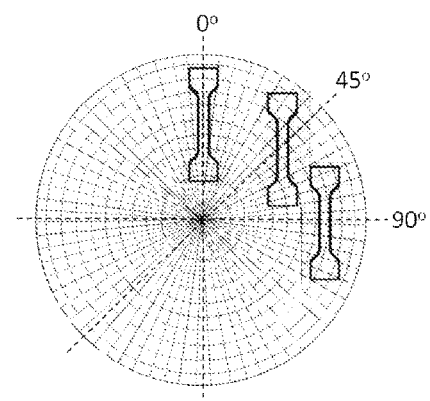
FIG. 8 is a diagram indicating the positions of samples taken for tensile testing.

The mechanical properties of such anisotropic samples have been investigated by means of tensile tests. By cutting out dog bone-shaped tensile bars at 0°, 45° and 90° with respect to the sample radius (shown in FIG. 8), three different angular arrangements of the microstructural orientation with respect to the stretching direction were measured. For comparison, samples having unidirectional orientation prepared by compression moulding in a channel die (see Stasiak et al. (2009) Macromolecules 42, 5256-5265 for method) were also prepared and stretched parallel (P) and normal (N) to the cylinders' orientation. The tensile tests were performed up to 0.5 strain (see Stasiak et al. (2009) Macromolecules 42, 5256-5265 for method). 8 samples of each orientation were measured for statistical purposes.

The tensile tests (FIG. 9) show mechanical anisotropy of the tested samples reflecting the microstructural anisotropy. The plotted stress is the true stress (force divided by the actual cross sectional area of the sample) and the strain $\varepsilon = \Delta L/L_0$, where $\Delta L$ is the increase of sample length and $L_0$ is the initial sample length. Two different injection rates have been considered: higher $7 \times 10^{-8}$ m$^3$s$^{-1}$ (FIGS. 9a-c, representing samples of thickness 0.95, 0.45 and 0.23 mm respectively) and lower $2 \times 10^{-8}$ m$^3$s$^{-1}$ (FIGS. 9d-f, representing samples of thickness 0.97, 0.44 and 0.30 mm respectively). In general for the higher injection rate the 0° samples are stronger than the diagonal (45°) followed by the 90°. While the differences between the stress-strain curves for the vertical, diagonal and horizontal specimens are insignificant for the 0.96 mm thick sample and higher injection rate, they became substantial for the smaller sample thicknesses and lower injection rate. For the 0.23 mm thickness and the higher injection rate, the stress-strain curves for 0° and 90° specimens very closely approach those for unidirectionally aligned P and N respectively. This suggests an increase of the radially oriented fraction over the circumferentially oriented fraction, in thinner samples. Given constant volumetric injection rate, the thinner samples have a higher flow rate between the plates. Consequently the contribution of the shear flow force to microstructure orientation becomes predominant. Conversely, for the lower injection rate and biggest space between plates, predominantly circumferential alignment is observed (FIG. 9d), resulting in 90° specimens being stiffer than 0° and 45° ones.

The fraction of the predominant orientation in each sample can be calculated by comparison of its elastic modulus (as an arithmetic average of initial modulus, 10%, 20%, 30% and 40% modules) to those of uniaxially oriented samples P and N. The integrated intensity of the principle X-ray diffraction peak was also used to quantify the proportion of each direction of orientation, for those samples for which X-ray data was available (those with the higher injection rate).

Computational fluid dynamics simulations provide more insight into the dynamic behaviour of the polymer during moulding, and allows identification of the mechanisms responsible for the microstructural anisotropy.

The flow system considered here cannot be solved analytically due to its non-linearity with respect to radius, depth and viscosity. Numerical modelling of the system has been carried out using ANSYS Polyflow. ANSYS solves the momentum and continuity equations at each finite element of a mesh. Incompressible, steady, continuous flow, with a purely viscous, 3-dimensional and isotropic medium was assumed.

Both shear and elongation can produce the forces necessary for orientation during flow of anisotropic morphologies in block copolymer systems. Elongation of spatial elements in the flow geometry of the samples originates from the circumferential growth of fluid elements as they move from the centre, to the outside of the discs (increasing radius). Shear forces are a result of creeping flow between narrow, non-slip plates. Thus, in this geometry, stretch and shear are orthogonal. This will also be true in many other injection moulding scenarios.

The modelling considers the ratio of shear rate to stretch rate, which is expressed as the dimensionless group $\psi = \gamma'/\varepsilon'$. It is hypothesised that there exists a constant critical value of $\psi$ below which stretch is dominant (resulting in circumferential orientation of cylinders), and above which shear is dominant (resulting in radial orientation of cylinders).

The development of the velocity profile between the thin plates is illustrated in FIG. 10a for 0.44 mm plate separation and $2 \times 10^{-8}$ m$^3$s$^{-1}$ injection rate. The non-parabolic flow profile is indicative of the non-Newtonian behaviour of the fluid. This profile results in the shear rates shown in FIG. 10b and the stretch rates shown in FIG. 10c. The stretch rate is dominated by circumferential terms. FIG. 10d shows the ratio of shear rate to stretch rate, $\psi$, believed to be the critical parameter in determining the orientation of cylinders. Four regions are indicated in FIG. 10d, and a horizontal line indicates the critical value. The regions are (I and IV) where shear is dominant, (II) where stretch due to biaxial elongation is dominant, and (III) where planar elongation occurs. Although $\psi$ varies across the depth of the sample it is almost constant at different radii; this explains why the orientation observed varies little with radius (see FIG. 4), except close to the injection point. The high ratio of shear to stretch near the surfaces accounts for the radial orientation of cylinders here. Towards the centre of the sample, the ratio of radial shear to stretch in the circumferential direction decreases, resulting in circumferentially oriented cylinders. Exactly at the centre, pure planar stretch is observed and this again results in circumferential orientation. Thus the modelling accounts for the SAXS patterns observed.

The modelling also accounts for the effect of a change in injection rate. With decreasing flow rate, and plate spacing held constant, the proportion of radial orientation predicted decreases. Consequently, the ratio of radial to circumferential orientation can be controlled in practical applications, for any given sample thickness.

With plate spacing reduced, and overall flow rate held constant, so that the fluid velocity increases, a more parabolic flow profile results, with a decreased region in which circumferential stretch dominates, and thus more shear (radial) orientation.

The ratio of radial to circumferential orientation calculated from the mechanical data can be matched by the modelling using a constant critical value of $\psi$=20 The fact that the critical value of $\psi$ is substantially greater than one shows that stretch is a significantly more efficient mechanism of orientation than is shear. At smaller values of $\psi$, stretch is dominant in determining the orientation of cylinders, whilst shear is dominant for larger values. Good agreement between the measured and computationally predicted fractions of radial orientation can be seen in Table 2.

TABLE 2

Fraction oriented radially calculated from mechanical, X-ray and numerical modelling data.

| Flow rate (m$^3$s$^{-1}$) | Plate separation (mm) | Mechanical testing | X-ray probing | Numerical modelling with a critical value of $\psi$ = 20 |
| --- | --- | --- | --- | --- |
| 2.00 × 10$^{-8}$ | 0.97 | 0.33 (±0.06) | 0.21 (±0.09) | 0.43 |
| 2.00 × 10$^{-8}$ | 0.44 | 0.56 (±0.04) | 0.50 (±0.08) | 0.66 |
| 2.80 × 10$^{-8}$ | 0.30 | 0.76 (±0.04) | 0.59 (±0.07) | 0.76 |
| 7.00 × 10$^{-8}$ | 0.95 | 0.48 (±0.05) | 0.51 (±0.05) | 0.47 |
| 7.00 × 10$^{-8}$ | 0.45 | 0.67 (±0.05) | 0.58 (±0.06) | 0.69 |
| 7.00 × 10$^{-8}$ | 0.23 | 0.86 (±0.10) | 0.63 (±0.08) | 0.83 |

Experiments (see FIG. 11) show that the formation of bi-directional orientation also occurs, as a result of injection moulding, for other block copolymers with cylindrical morphology, such as poly (styrene-block-isoprene-block-butadiene-block-styrene) having 19% wt styrene (SI-BS19) or poly(styrene-block-isobutylene-block-styrene) with 30% wt styrene (SIBS30). All cylinder forming materials tested formed layers of orthogonally oriented cylinders similar to those described in detail in this paper for SIS30. Rheological differences between the different materials result in different detailed patterns of orientation for different materials under the same processing conditions. These differences can be satisfactorily explained by modelling of the type described above, inputting only simple shear rheological measurements. It is thus possible to predict and control the microstructure formed by an interaction of the material being injected, the injection geometry and the processing conditions, including injection rate and temperature.

Application to Heart Valves

The above discussion has shown that it is possible to predict and control the formation of the bi-directional orientation during processing. As such, processes for manufacturing synthetic heart valves from block copolymers can be controlled to take advantage of the bidirectional orientation. Effectively, the phase structure is arranged in layers, with the nanophases differently aligned in the neighbouring layers. This is at least visually similar to the network of tissue in a native heart valve leaflet, which is suggestive that a synthetic leaflet with the bidirectional structure will have behave in a similar way to a natural leaflet. The bidirectional structure also helps to reinforce the leaflets where they are attached to the surrounding valve, which are the regions in which a mechanical failure was hitherto most likely, thereby making the overall valve more robust.

In fact, through computer modelling, the optimal injection location(s) for performing injection moulding can be determined, based on modelling the stresses in a particular valve shape made of a particular material, and optimising the injection location to minimise the concentration of those stresses (the change in injection location influencing the concentration of the stresses due to the change in location producing a change in the flow patterns and therefore final nanophase orientation in the moulded valve). In practice, such modelling might be limited to a valve leaflet, or half a leaflet (due to the symmetrical nature of the leaflets), to identify the injection position that minimises the stress concentration experienced by the leaflet in use.

FIG. 12 shows the basic structure of a prosthetic heart valve. The body of the valve 110 comprises a stent 111 with three posts 112 supported on a base 113. Three valve leaflets 114 each extend between and connect to two of the posts 112, with base of each leaflet attached to the base 113 between the two posts to which it is connected. The leaflets 114 are for actuating the valve.

The leaflets are shaped so that their tops meet in the middle of the valve 110. In use, blood flow from below (in the orientation of FIG. 11) the valve 110 will cause the leaflets to separate and allow the blood to pass through the valve 110, whereas any attempted flow in the other direction will force the leaflets 114 towards each other and thus close the valve 110.

The entire valve shown in FIG. 11 can be manufactured in a single step, by injection moulding, resulting in a valve formed of a single material without any joints between parts. Producing the valve 110 as a single piece is advantageous, because it avoids the formation of any weak areas where pieces are joined together. Therefore, the valve 110 is more robust if it is a single piece. However, the heart valve may include non-injection moulded elements (for example an underlying or supporting scaffold for the injection moulded element), which may be made of a different material to the injection moulded material. Preferably, the valve leaflets 114 are made by injection moulding BCP.

The thickness of the valve leaflets 114 is preferably in the range of from 0.15 to 0.55 mm, for optimal performance, and more preferably 0.2 to 0.5 mm, still more preferably 0.3 to 0.4 mm and most preferably around 0.35 mm. The posts 112 are thicker in order to provide support for the leaflets 114.

The valve 110 can be any type of prosthetic heart valve, e.g. a transcatheter heart valve.

The valve 110, particularly the valve leaflets 114, have anisotropic physical properties on the macroscopic scale. This is because, as discussed above, the injection moulding process causes the BCP to aligned bidirectionally at the local level (or microscopic scale). The skilled reader will understand that the direction of the orientation in an absolute frame of reference will vary at different points on the leaflet due to the shape of the leaflet and the location of the injection moulding points in the mould (e.g. for the samples discussed above 'surface' orientation occurs radially, and so in different absolute directions at different points on the sample). Nonetheless, at the microscopic scale, the bidirectional orientation (in which the phase structure in the central layer is aligned substantially perpendicularly to the phase structure in the outer two layers) will be present, and at the macroscopic scale anisotropic properties are manifested (i.e. the variation in absolute alignment is not so varied as to be random—which would then result in isotropic properties). In particular, the Young's modulus is anisotropic.

Examples of such orientation are shown in FIGS. 13-15. In each of these figures, part (a) shows the modelled injection velocity profile (i.e. the expected flow paths of the polymer during injection), parts (b) and (c) show SAXS images taken from two leaflets of a single valve and part (d) shows the phase structure predicted via modelling. Each figure shows the BCP phase orientation for SIS30 injection moulded into a heart valve leaflet, with a different injection geometry: FIG. 13 shows point injection, centrally at the top of the leaflet (experimental barrel injection barrel pressure 85.1 bar; experimental injection rate 6.2 mm³/s; modelled die inlet pressure 34.5 bar); FIG. 14 shows point injection at the commissures (experimental barrel injection barrel pressure 64.5 bar; experimental injection rate 12.1 mm³/s; modelled die inlet pressure 11.6 bar); and FIG. 15 shows continuous injection along the whole top edge of the leaflet (experimental barrel injection barrel pressure 49 bar; experimental injection rate 17 mm³/s; modelled die inlet pressure 15.7 bar).

Vectors for core and surface orientation of the cylindrical phase structures are shown in part (d) of each figure. It should be noted that there is an apparent asymmetry in these part (d) images, but this is an artefact of the fact that the model does not distinguish any given direction from a direction 180 degrees rotated (since these are effectively the same for a cylindrical phase structure). Also, edge effects give rise to some anomalous vectors. However, it can be seen, the overall direction of orientation at any point on the leaflet varies, but the core and surface orientations frequently remain substantially perpendicular. That is, at any given point, the phase structures are substantially perpendicular to each other at the boundary between layers.

Parts (b) and (c) of each figure show the experimentally determined orientation for injection moulded leaflets under similar conditions to those defined in the calculations. In each case two leaflets were cut out from the valve, flattened and the orientation mapped using X-ray diffraction (due to time constraints only roughly half of each leaflet was mapped—the other half should be approximately symmetrical). Measurements of the thickness of each leaflet at three points (Left, Bottom and Right) were 0.38, 0.30, 0.36 mm for FIG. 13b; 0.31, 0.29, 0.33 mm for FIG. 13c; 0.30, 0.25, 0.48 mm for FIG. 14b; 0.32, 0.39, 0.35 mm for FIG. 14c; 0.36, 0.14, 0.28 mm for FIG. 15b; and 0.38, 0.10, 0.22 mm for FIG. 15c. Modelling for part (d) was performed using a constant thickness of 0.35 mm for each scenario. The variation in orientation distribution between leaflets from the same valve and the differences to the calculated distributions can be attributed to the variation in leaflet thickness. It is clear that the modelling gives a reasonable description of the orientation distribution achieved and that control of orientation can be achieved using injection geometry (and processing parameters). Thus orientation with in a heart valve leaflet can be both predicted and controlled.

In order to obtain the desired bidirectional orientation in the block copolymer, it is preferable to position the injection moulding points on the axis of symmetry 114 of each leaflet. In particular, the top and/or base of each leaflets are preferred injection points for promoting optimal orientation and also ensuring even flow of the injection moulding material through the valve mould. Preferably, the pure polymer is injection moulded. In particular, the polymer is preferably not combined with a lubricant (e.g. for assisting in the moulding step). Also, the polymer is preferably not combined with any solvent.

The particular block copolymers used for the injection moulding preferably form the cylindrical phase structure. In particular, those with a 'glassy' (i.e. a polymer which is above its glass transition temperature at body temperature—for example polystyrene) phase forming the cylinders in a 'rubbery' (i.e. a polymer which is below its glass transition temperature at body temperature) matrix are preferred for their. The block copolymers are also desirably biocompatible, and as such a saturated component forming the rubbery matrix is preferred for chemical stability. However, unsaturated components may also be used if they provide a high enough chemical stability.

Preferred block copolymers for use in forming the heart valve include SIBS30 (poly(styrene-block-isobutylene-block-styrene), 30% styrene); SIS30 (poly(styrene-block-isoprene-block-styrene), 30% styrene); SI/BS19 (poly(styrene-block-isoprene/butadiene-block-styrene), 19% styrene); SIS18 (poly(styrene-block-isoprene-block-styrene), 18% styrene); SE/BS30 (poly(styrene-block-ethylene/butylene-block-styrene), 30% styrene); SE/BS20 (poly(styrene-block-ethylene/butylene-block-styrene), 20% styrene); SE/PS20 (poly(styrene-block-ethylene/propylene-block-styrene), 20% styrene); and SE/PS22 (poly(styrene-block-ethylene/propylene-block-styrene), 22% styrene).

Of the polymers listed above, those with a styrene content of 18 to 22% are preferred for their mechanical properties. SE/PS20, SE/PS22 and SE/BS20 are particularly preferred.

The injection moulding process is carried out below the order-disorder transition temperature. Within this constraint, a high temperature aids the flow of the polymer through the mould. Conversely, if the injection moulding apparatus is not operated under an inert atmosphere, lower temperatures have an advantage of avoiding undesirably oxidation.

However, these considerations are both tempered by the fact that modelling suggests that higher temperature injection (i.e. with low polymer viscosity) results in a larger depth of 'surface' orientation (and thus a reduced thickness of the 'central' orientation). Another factor, as demonstrated above, affecting the relative amounts of the two orientations includes the injection rate (lower injection rate flavouring larger amounts of 'surface' orientation). The specific polymer being used will also affect the relative amount of each orientation seen.

As such, the optimal operating conditions will vary from polymer to polymer, but a combination of processing temperature, injection rate, injection position and the material being injected can be used to control the structure produced.

In general, the amount of surface orientation in the leaflets (expressed as a percentage of the overall leaflet thickness, and including both surfaces) is preferably in the range of 40 to 60%, more preferably around 50%, but could be in the range of from 25 to 75%. In particular, using an injection point at the top of the leaflets, optimal mechanical properties are achieved with lower proportions of surface orientation, whereas a bottom injection point produces better results with a higher proportion of surface orientation.

However, in some applications, it may be desirable to use the injection moulding method to obtain a product with almost 100% of a particular orientation e.g. by processing either very quickly, to obtain alignment in a primarily 'radial' shape from an injection point, or by processing slowly to obtain alignment in a primarily 'circumferential' shape around the injection point (it will be appreciated that the terms 'radial' and 'circumferential' are not used in the strict sense, because complex mould geometries will give rise to complex orientation patterns—as such the term 'radial' is used to mean the orientation in the 'surface' layers, whilst the term 'circumferential' is used to refer to the orientation in the inner layer). That is, the processing conditions can be controlled to primarily obtain one particular orientation, e.g. 90% or more of one orientation, or even 95% or more of one orientation layer (or, put another way, 10% or less of one orientation, or even 5% or less of one orientation layer). In particular, since the 'circumferential' orientation cannot be achieved by conventional compression moulding, it may be desirable to produce materials by injection moulding that have close to 0% surface orientation.

The injection moulding for forming the block copolymer can generally be described as follows. The injection moulding apparatus, including the mould, is prepared and preferably placed under an inert atmosphere. The cylinder-forming block copolymer is injected moulded into the mould, at a temperature below the order-disorder transition temperature. This is to preserve an arrangement of the phase structure created during the step of injection moulding and produce the desired anisotropic physical properties in the heart valve.

Although the preceding discussion has focussed on applications in heart valves, the bidirectionally aligned BCP material can be used in other applications. For example, the material could be used to create (i.e. non-prosthetic) valves for controlling liquids in other applications. Alternatively, the material could be used in other prosthetic applications. For example, another instance of a native tissue with a bi-directional microstructure alignment is the outer coating of the eye, the cornea stroma. The cornea contains several overlapping layers composed of bundles of collagen fibrils surrounded by a soft matrix of glycoprotein. The collagen fibrils of 25-35 nm diameters run parallel to each other with somewhat regular spacing, forming a layer (lamella). Lamellae about 200 μm thick each are crosswise stacked. The existence of parallel to the surface, but orthogonally to each other, oriented layers of collagen fibrils is responsible for the ability of the cornea to transmit light, while being mechanically resilient. Anisotropy in stromal architecture also results in mechanical anisotropy. It has been demonstrated that specimens extracted from the vertical direction of cornea were up to 20% stronger than horizontal specimens. It is believed that such microstructure allows maintenance of corneal strength and curvature. Therefore, a bidirectionally aligned BCP material could be used to create a prosthetic cornea, mimicking the native structure.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A heart valve having at least a portion thereof constructed from a block-copolymer having at least first constituent blocks and second constituent blocks, the block-copolymer having first phase structures formed by the first constituent blocks and a second phase structure formed by the second constituent blocks,
   wherein the first and second phase structures are arranged so as to produce anisotropic physical properties in the at least the portion of the heart valve constructed of the block copolymer,
   the first phase structures formed by the first constituent blocks are dispersed throughout the second phase structure formed by the second constituent blocks, the second phase structure defining a total thickness of the portion of the heart valve,
   a first group of the first phase structures formed by the first constituent blocks are dispersed in the second phase structure such that each of the first phase structures of the first group are aligned in a first direction, and a second group of the first phase structures formed by the first constituent blocks are dispersed in the second phase structure such that each of the first phase structures of the second group are aligned in a second direction that is different from the first direction, and
   the first group is located throughout a first thickness of the total thickness of the second phase structure, and the second group is located throughout a second and separate thickness of the total thickness of the second phase structure.

2. The heart valve according to claim 1, wherein the heart valve comprises leaflets for actuating the valve, and the leaflets are made from the block-copolymer with the arranged phase structures.

3. The heart valve according to claim 1, wherein the first phase structures are comprised of cylinders of the first constituent blocks that are formed of a first polymer material of the block-copolymer in a matrix of a second polymer material of the block-copolymer that forms the second phase structure.

4. The heart valve according to claim 3, wherein the first polymer material of the block-copolymer is a glassy polymer at body temperature and the second polymer material of the block-copolymer is a rubbery polymer at body temperature.

5. The heart valve according to claim 4, wherein the block-copolymer is one of SIBS30 (poly (styrene-block-isobutylene-block-styrene), 30% styrene); SIS30 (poly (styrene-block-isoprene-block-styrene), 30% styrene); SI/BS19 (poly (styrene-block-isoprene/butadiene-block-styrene), 19% styrene); SIS18 (poly (styrene-block-isoprene-blockstyrene), 18% styrene); SE/BS30 (poly (styrene-block-ethylene/butylene-block-styrene), 30% styrene); SE/BS20 (poly (styrene-block-ethylene/butylene-block-styrene), 20% styrene); SE/PS20 (poly (styrene-block-ethylene/propylene-block-styrene), 20% styrene); and SE/PS22 (poly (styrene-block-ethylene/propylene-block-styrene), 22% styrene).

6. The heart valve according to claim 1, further comprising a third group of the first phase structures formed by the first constituent blocks that are dispersed in the second phase structure such that each of the first phase structures of the third group are aligned in the first direction, the third group is located throughout a third thickness of the total thickness of the second phase structure that is separate from each of the first and second thicknesses, and the first and third groups of the first phase structures sandwich the second group of the first phase structures.

7. The heart valve according to claim 6, wherein a sum of the first and third thicknesses is from 25% to 75% of the total thickness of the second phase thickness.

8. The heart valve according to claim 6, wherein the first direction is perpendicular to the second direction.

9. A method of manufacturing the heart valve according to claim 1, the method comprising:
   a step of injection moulding at least one part of the heart valve from the block-copolymer, wherein the injection moulding is performed at a temperature below an order-disorder transition temperature for the block copolymer, such that the first and second phase structures are present in the molten block-copolymer; and
   a step of cooling the at least one part of the heart valve after it is moulded, without heating the at least one part above the order-disorder transition temperature between the step of injection moulding and the step of cooling, so as to preserve an arrangement of the first and second phase structures created during the step of injection moulding and produce the anisotropic physical properties in the heart valve.

10. The method of manufacturing the heart valve according to claim 9, wherein the step of injection moulding includes use of a mould with injection moulding points positioned at a top and/or base of one or more leaflets of the heart valve.

11. The method of manufacturing the heart valve according to claim 9, further comprising designing a mould for the method of manufacturing the heart valve, wherein designing of the mould comprises:
   modelling at least a section of the at least one part of the heart valve produced by the mould, including modelling stresses in the valve and accounting for an orientation of the first phase structures within the second phase structure;
   changing an injection position of the block copolymer in the model of the mould, and remodeling the at least a section of the at least one part of the heart valve;
   selecting the injection position, based on the modelling and remodeling, that provides the least stress concentration in the valve; and
   producing the mould with the injection position in the position that provides the least stress concentration in the valve.

12. A method of producing anisotropic physical properties in the heart valve at least partially constructed from the block copolymer according to claim 1, the method comprising:
   a step of injection moulding the block-copolymer at a temperature below an order-disorder transition temperature for the block copolymer, without lubricant, such that the first and second phase structures are present in the molten block-copolymer; and
   a step of cooling the molten block-copolymer after it is moulded, without heating the block-copolymer above the order-disorder transition temperature between the step of injection moulding and the step of cooling, so as to preserve an arrangement of the first and second phase structures created during the step of injection moulding and to produce the anisotropic physical properties in the heart valve.

\* \* \* \* \*